United States Patent [19]
Berndt

[11] Patent Number: 5,498,543
[45] Date of Patent: Mar. 12, 1996

[54] SUB-COMPACT BLOOD CULTURE APPARATUS

[75] Inventor: Klaus W. Berndt, Stewartstown, Pa.

[73] Assignee: Becton Dickinson and Company, Franklin Lakes, N.J.

[21] Appl. No.: 255,195

[22] Filed: Jun. 7, 1994

[51] Int. Cl.⁶ ............................................. C12M 1/34
[52] U.S. Cl. .................. 435/286.1; 422/63; 422/82.8;
356/39; 356/427; 356/435; 435/286.2; 435/287.3;
435/303.1
[58] Field of Search ................... 422/62, 67, 82.05,
422/82.08; 435/284, 291, 312; 356/39,
427, 435

[56] References Cited

U.S. PATENT DOCUMENTS

| | | | |
|---|---|---|---|
| 3,928,140 | 12/1975 | Wyatt et al. | 195/103.5 |
| 4,152,213 | 5/1979 | Ahnell | 195/103.5 M |
| 4,576,916 | 3/1986 | Lowke et al. | 435/289 |
| 4,672,038 | 6/1987 | Jaekel et al. | 435/291 |
| 4,889,992 | 12/1989 | Hoberman | 250/343 |
| 4,940,332 | 7/1990 | Miwa et al. | 356/417 |
| 4,945,060 | 7/1990 | Turner et al. | 435/291 |
| 4,952,498 | 8/1990 | Waters | 435/34 |
| 4,971,900 | 11/1990 | Ahnell et al. | 435/29 |
| 5,110,743 | 5/1992 | Windisch et al. | 436/48 |
| 5,134,623 | 7/1992 | Egawa et al. | 372/31 |
| 5,155,019 | 10/1992 | Sussman et al. | 435/34 |

OTHER PUBLICATIONS

Thorpe et al., "BacT/Alert: an Automated Colorimetric Microbial Detection System," Journal of Clinical Microbiology, Jul. 1990, pp. 1608–1612.

Primary Examiner—David A. Redding
Attorney, Agent, or Firm—Alan W. Fiedler

[57] ABSTRACT

The present invention describes an apparatus for detecting biological activities in a large number of blood culture vials. The vials are placed in a plurality of arcuate shaped drawers that together form a drum that is rotated about a central horizontal axis. In one preferred embodiment, the apparatus includes five drawers with each drawer containing forty-eight vials. The apparatus includes a door on the front that opens and permits the lower drawer to be removed from the apparatus by lab personnel to load the entire drawer with up to forty-eight vials and unload the same when necessary from the top of the drawer. Another embodiment has an indicator associated with each vial in the drawer to provide additional information to lab personnel about the status of each vial in the drawer.

10 Claims, 8 Drawing Sheets

SUB-COMPACT BLOOD CULTURE APPARATUS

BACKGROUND OF THE INVENTION

1. Field of the Invention

The present invention relates to a non-invasive apparatus for detecting biological activities in a specimen such as blood, where the specimen and a culture medium are introduced into a large number of sealable containers and then exposed to conditions enabling a variety of metabolic, physical, and chemical changes to take place in the presence of microorganisms within the sample.

2. Background Description

The presence of biologically active agents such as bacteria in a patient's body fluid, especially blood, is generally determined using blood culture vials. A small quantity of blood is injected through an enclosing rubber septum into a sterile vial containing a culture medium, and the vial is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different vials. It has also been proposed to detect microorganism growth in sealable containers by monitoring positive and/or negative pressure changes.

Recently, non-invasive methods have been developed involving chemical sensors disposed inside the vial. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each vial. This results in station sensitivity variations from one vial to the next. Therefore, extensive and time-consuming calibration procedures are required to operate such systems. In addition, flexible electrical cables are required to connect the individual sources and detectors with the rest of the instrument. With the large number of light sources, typically 240 or more per instrument, maintenance can become very cumbersome and expensive when individual sources start to fail.

In known colorimetric or fluorometric instruments, light emitting diodes ("LEDs") are used as the individual light sources. These sources have only a relatively low optical output power. Therefore, high photometric detection sensitivity is required to monitor the vial sensor emissions. This results in additional and more complicated from-end electronics for each photodetector, increasing production cost. To reduce equipment cost and complexity, it has been proposed to use optical fibers at each vial to feed the output light of an instrument's sensors to a central photodetector. A disadvantage to this approach is the need for arranging a large number of relatively long fibers of different length within the instrument.

It has also been proposed to introduce a culture medium and blood specimen into each sealable glass vial having an optical sensing means and a barcode label. Arranging a large number of these vials radially on a rotating drum within an incubator and mounting sensor stations in the instrument at a predetermined distance from the drum so that during rotation of the drum each individual vial is passing over a sensor station. In that type of system, the inner bottom of each vial is covered with a fluorescent chemical sensor and a linear barcode label is attached to one side of each vial. The vials are then arranged radially on a rotating drum within the incubator, with each vial neck oriented towards the drum axis and all the vials located in groups on disk-like segments with each vial reaching only partially into the drum so that the barcode labels are accessible for scanning.

To load and unload this apparatus, however, the user must grasp each vial at its base and feed it into the drum neck-first. In known automated non-invasive blood culture systems, vials are commonly transported to the automated blood culture apparatus in an upright orientation, therefore, each vial must be grasped twice before loading. The need to grasp each vial twice to load each vial neck-first into the drum requires additional work. Because microbiology lab personnel are accustomed to grasping vials at the neck, there is a need to overcome the unusual situation of feeding blood culture vials into the system neck-first. In addition, the apparatus must be loaded a vial at a time, which also is very time consuming.

SUMMARY OF THE INVENTION

The present invention overcomes the above problems and comprises a sub-compact blood culture apparatus for detecting biologically active agents in a large number of blood culture vials that is simple and can be produced at very low cost. It incorporates individual vial identification and the application of more than one microorganisms detection method within a single instrument. The apparatus provides low system sensitivity variations from one vial station to the next and does not require electronic or optoelectronic components, electrical wires, or optical fibers on a moving dial rack. As a result of these several advantages, it provides long-term reliability during operation.

In addition, the present invention allows lab personnel to grasp each vial at its neck during loading and unloading, offers simultaneous access to a large number of vials during loading and unloading, and also has a smaller footprint as compared to existing blood culture systems without any increase in height.

According to the present invention, a culture medium and blood specimen are introduced into sealable glass vials containing optical sensing means and having a bar code pattern for individual vial identification associated thereto. A large number of such vials are arranged radially on a rotatable drum within an incubator, which is used to promote microorganism growth. Sensor stations are mounted to the mainframe of the blood culture apparatus at such a distance from the drum that, during its rotation, each individual vial passes over a sensor station.

In a first embodiment of an apparatus according to the present invention, the vials are arranged radially on a rotatable drum within an incubator. The shaft or axis of the rotatable drum is oriented horizontally and perpendicular to the front face of the incubator. To load and unload each vial into and out of the drum, the front face of the incubator has a door in its lower area. A preferred arrangement of the vials on the drum is to group the vials using disk-like segments around the axis in a number of equal subdivisions that carry arcuate shaped drawers with openings for the vials.

Each disk-like segment or drawer is mounted on rails that are oriented parallel to the drum's axis. During the loading and unloading operations, the drum is rotated until one drawer is located at the door in the incubator's front face. The drum is then stopped, the door opened, and the corresponding drawer of vials is moved through the door out of the incubator on the rails. For example, if the drum contains eight disk-like segments of thirty vials each and is segmented into five subdivisions, then one drawer would contain 48 openings to accepted 48 blood culture vials. Each of the vials are loaded and unloaded in an upright orientation from the top of the drawer, since the door is located in the lower drum area. Of course, to access the remaining vial drawers, the first drawer is moved back into the incubator on the rails, the door is closed, the drum is rotated through an angle of 72°, the door is again opened, and the next drawer is moved out of the incubator on the rails.

Another embodiment of the present invention uses only three automated drawers having 80 vial stations therein. Therefore, it is easier for lab personnel to load and unload the apparatus since the user has access to 80 vial stations, simultaneously, and the whole loading and/or unloading operation requires only three steps.

These and other aspects, features and advantages of the present invention will become apparent from the following detailed description, taken in conjunction with the accompanying drawings.

DETAILED DESCRIPTION

Figure 1:
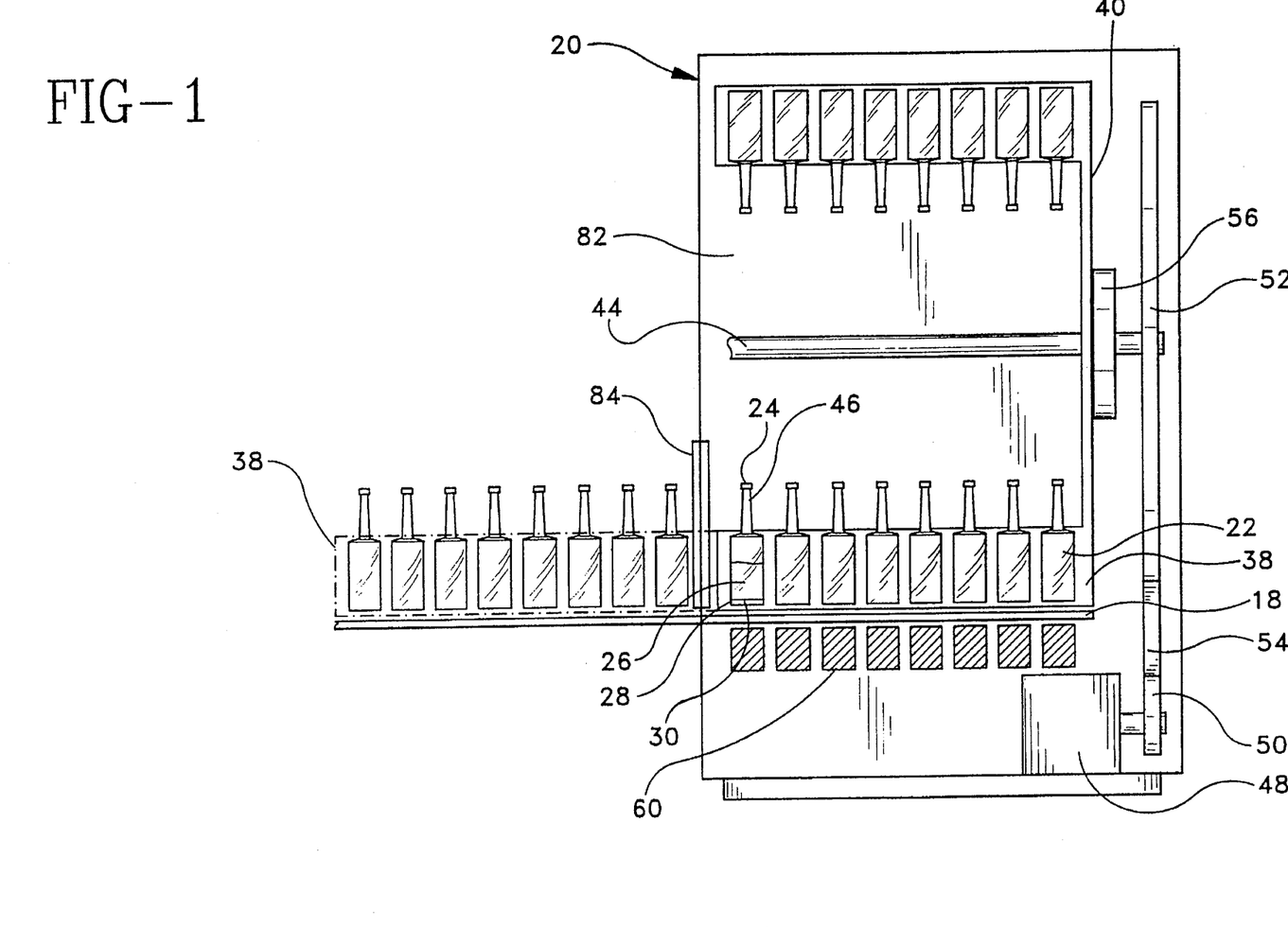
FIG. 1 shows a side view of the interior of a sub-compact blood culture apparatus for the detection of microorganisms according to the present invention, with an embodiment comprising eight disk-like drum segments with thirty vials in each segment.

A sub-compact blood culture apparatus 20 embodying the principles and concepts of the present invention is depicted schematically in FIG. 1. Apparatus 20 comprises a drum 40 containing a plurality of glass vials 22, each sealed with a septum 24 and containing a medium/blood mixture 26. Each vial 22 contains a fluorescence chemical sensor 28 disposed on an inner bottom surface 30, and a bar code label (not shown) positioned on bottom surface 30.

In one preferred embodiment, a drum shaft 44 is oriented horizontally with respect to the front of apparatus 20, and vials 22 are oriented with their necks 46 toward drum shaft 44. In this way, the force of gravity efficiently agitates medium/blood mixture 26 as drum 40 rotates. Of course, the present invention is not limited to an apparatus with such an orientation.

Rotation of drum 40 is accomplished by a stepper motor 48 which is connected to drum 40 by toothed drive pulleys 50 and 52, and a toothed drive belt 54. Drum 40 is arranged within an incubator 82, shown in FIG. 2, to promote microorganism growth within vials 22. The actual orientation of drum 40 is then monitored through the use of a location positioner such as an angular encoder 56 mounted to shaft 44.

A plurality of sensor stations 60 are secured to a portion of apparatus 20 at such a distance from drum 40 that during its rotation individual vials 22 pass over a sensor station 60. In the preferred embodiment shown in FIG. 1 at least eight sensor stations 60 are used, with sensor station 60 testing each vial 22 for the concentration of $CO_2$ gas as each vial 22 passes over sensor station 60. Preferably, each sensor station 60 includes a light source that generates and directs light towards the fluorescence chemical sensor 28 in each vial 22. Sensor 28 then emanates differing quantities of light depending upon the amount of $CO_2$ detected by sensor 28. For example, the more $CO_2$ in vial 22, the more light is emanated from sensor 28. The emitted light is then received by sensor station 60, which then transmits signal data to a display 31, shown in FIG. 3, concerning the presence or absence of biologically active agents, such as bacteria, in each vial 22. It should be understood, of course, that the use of a $CO_2$ sensor is not required to practice the present invention, since other non-invasive means could be used to detect $CO_2$ within vial 22, e.g., a scattered photon migration (SPM) technique. In addition, two or more detection principles could also be applied, but would require more sensor stations 60 in each drawer 38.

As discussed further below, drawers 38 do not contain electronic or optoelectronic components, and no flexible electrical cables or optical fibers are required. Therefore, an apparatus according to the present invention can be produced at reduced cost compared to existing blood culture instruments. The drum concept allows for high density packaging, particularly with neck 46 disposed into drum 40. The inventor has determined that this arrangement increases package density by a factor of approximately two and a half when compared to prior art devices. Therefore, smaller instruments can be built and by varying the number of drawers 38 instruments with small, medium, or large vial numbers are possible.

Figure 2:
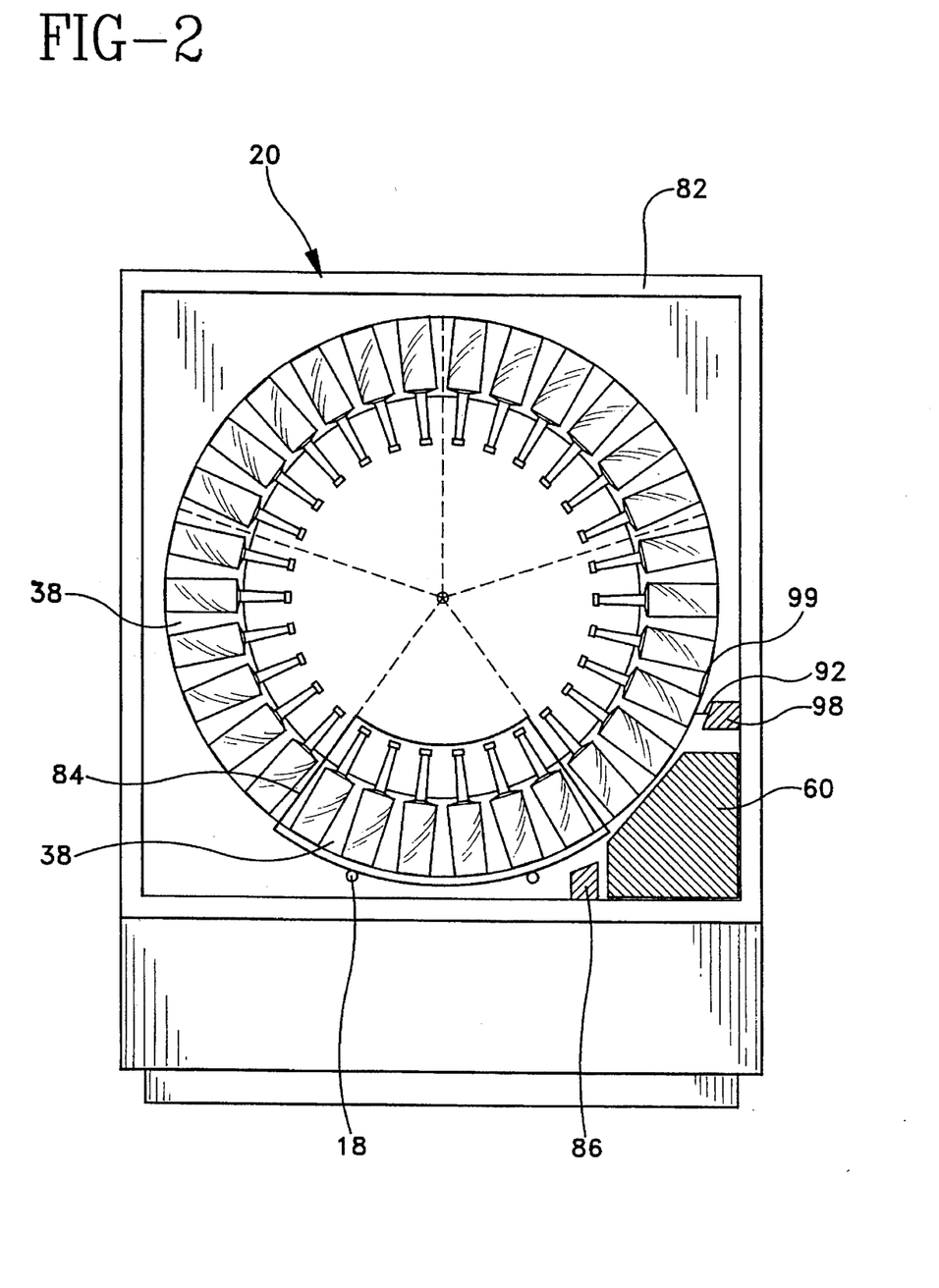
FIG. 2 shows a cross-sectional front view of the apparatus shown in FIG. 1.

FIG. 2 shows a cross-sectional front view of the interior of blood culture apparatus 20. Apparatus 20 includes five drawers 38 that can be slid out of and into apparatus 20 during loading and unloading on rails 18 through a door 84, shown in FIG. 3. Each drawer 38 holds forty-eight vials 22 in a matrix of openings having six rows and eight columns. Therefore, apparatus 20 when fully loaded can hold two hundred and forty vials 22.

FIG. 2 also shows a bar code reader 86 for each sensor station 60. During drum rotation, all vials 22 pass by respective barcode readers 86 to allow reader 86 to scan the bar code label on each vial 22 and identify each vial 22. An auxiliary optoelectronic sensor 98 associated with each sensor station 60, receives a light pulse whenever a portion of each vial 22, and particularly its bottom 99, pass through beam 92. In this way, the presence of vial 22 in an opening located over sensor station 60 can be verified. It is also envisioned that auxiliary optoelectronic sensor 98 and bar code reader 86 may be used as a supplement for or in place of encoder 56, shown in FIG. 1, as a location positioner for drum 40. When it is determined that a vial 22 is positioned over sensor station 60, the process of detecting microorganism growth in vial 22 is performed by sensor station 60 and the results are displayed on display 31, shown in FIG. 3.

Figure 4:
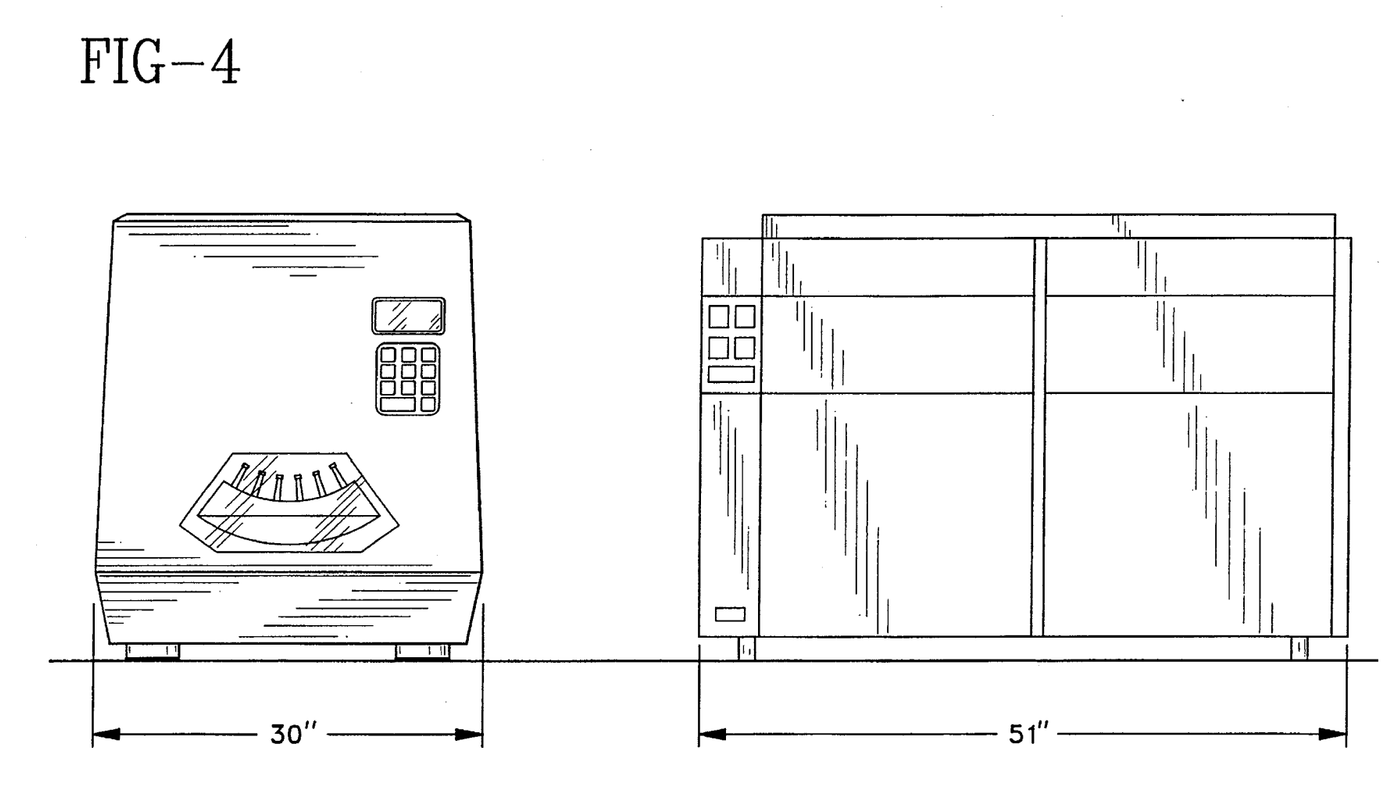
FIG. 4 shows a perspective view of the 240-vial blood culture apparatus shown in FIG. 1, according to the present invention, in comparison to an existing 240-vial blood culture apparatus (BACTEC 9240® Blood Culturing System, currently sold by Becton Dickinson and Company)

Such an arrangement provides for individual identification of each vial 22 within apparatus 20 by bar code labels and can provide more than one microorganism-detection method within apparatus 20. It also provides low sensitivity variations from one vial 22 to the next and does not require electronic or optoelectronic components on the vial drawer 38. The present invention also overcomes the man-machine interface problem caused when vials had to be grasped at the bottom and fed into the system neck-first. In addition, the present invention offers simultaneous access to all forty-eight vials in drawer 38 during loading and unloading. In addition, as shown in FIG. 4, the new two hundred and forty vial system has a footprint that is 41% smaller than the footprint of the BACTEC 9240® system currently being sold by Becton, Dickinson and Company, without increasing height, as discussed below.

Figure 3:
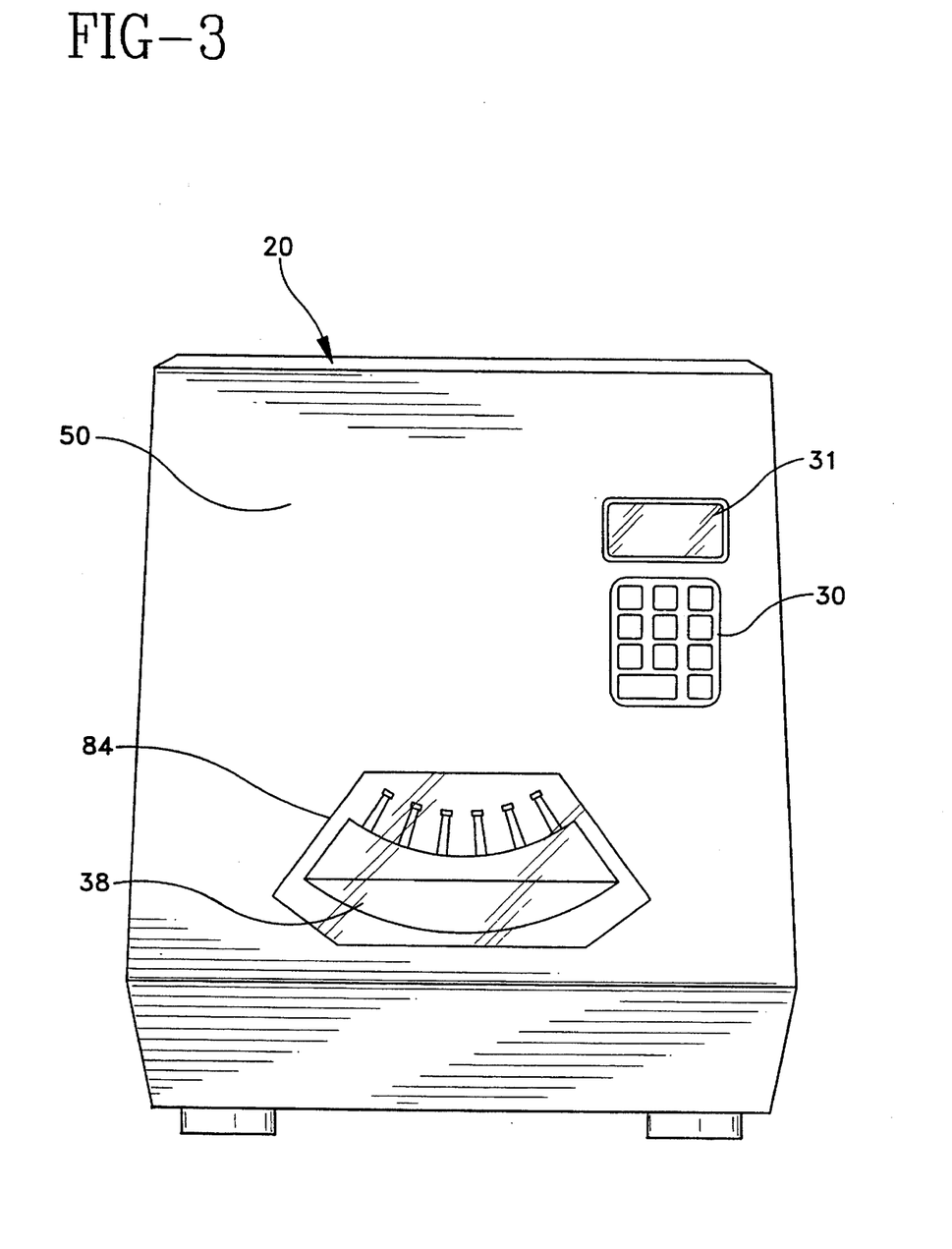
FIG. 3 shows a full front view of the apparatus shown in FIGS. 1 and 2.

FIG. 3 shows a full front view of blood culture apparatus 20, and more clearly shows door 84 that receives each drawer 38 containing forty-eight vials 22. In addition, FIG. 3 shows a control panel 30 used to control apparatus 20 and display 31 for displaying information about the operation of apparatus 20 on the front face 50 of blood culture apparatus 20. FIG. 4 clearly shows the difference between the currently available BACTEC 9240® system and apparatus 20 of the present invention and, more particularly, shows the length of apparatus 20 to be 30 inches, which is smaller than the length of the currently available BACTEC 9240® system that is 51 inches. The present invention, therefore, reduces the overall footprint but still cultures two hundred and forty vials 22.

Figure 5:
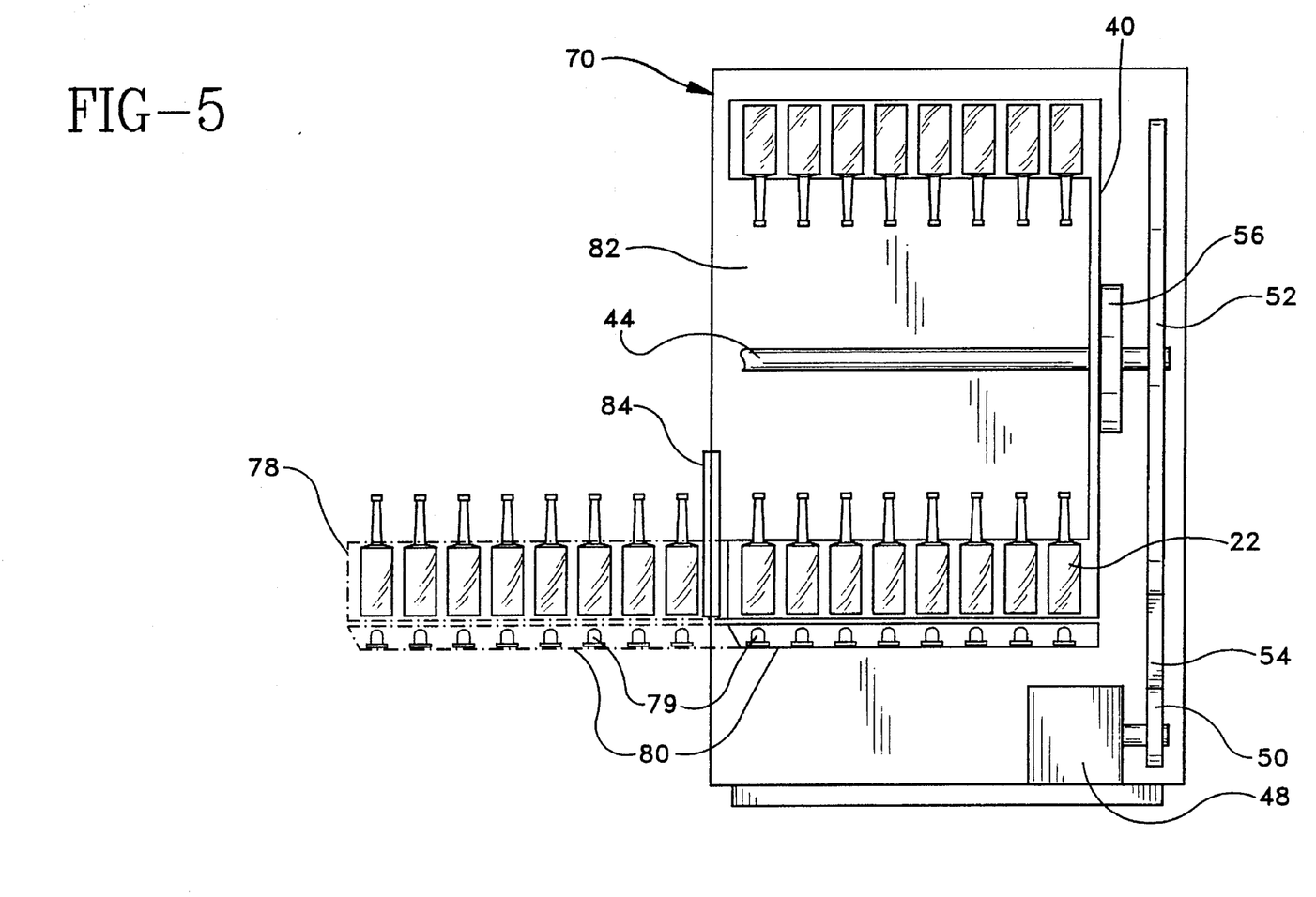
FIG. 5 shows an alternative embodiment of a sub-compact blood culture apparatus according to the present invention with a lower automated drawer having 48 LED's as illumination sources for 48 load/unload indicators.

FIG. 5 shows another embodiment of a blood culture apparatus 70 according to the present invention, with components similar to components in apparatus 20 represented by the same numerals. Blood culture apparatus 70 includes an additional lower drawer 80 with forty-eight LED's 79 as illumination sources serving as load/unload indicators that indicate whether a corresponding vial contains bacteria or not. Lower drawer 80 moves together with upper automated drawer 78 out of door 84 in incubator 82 during loading/unloading operations.

Figure 6:
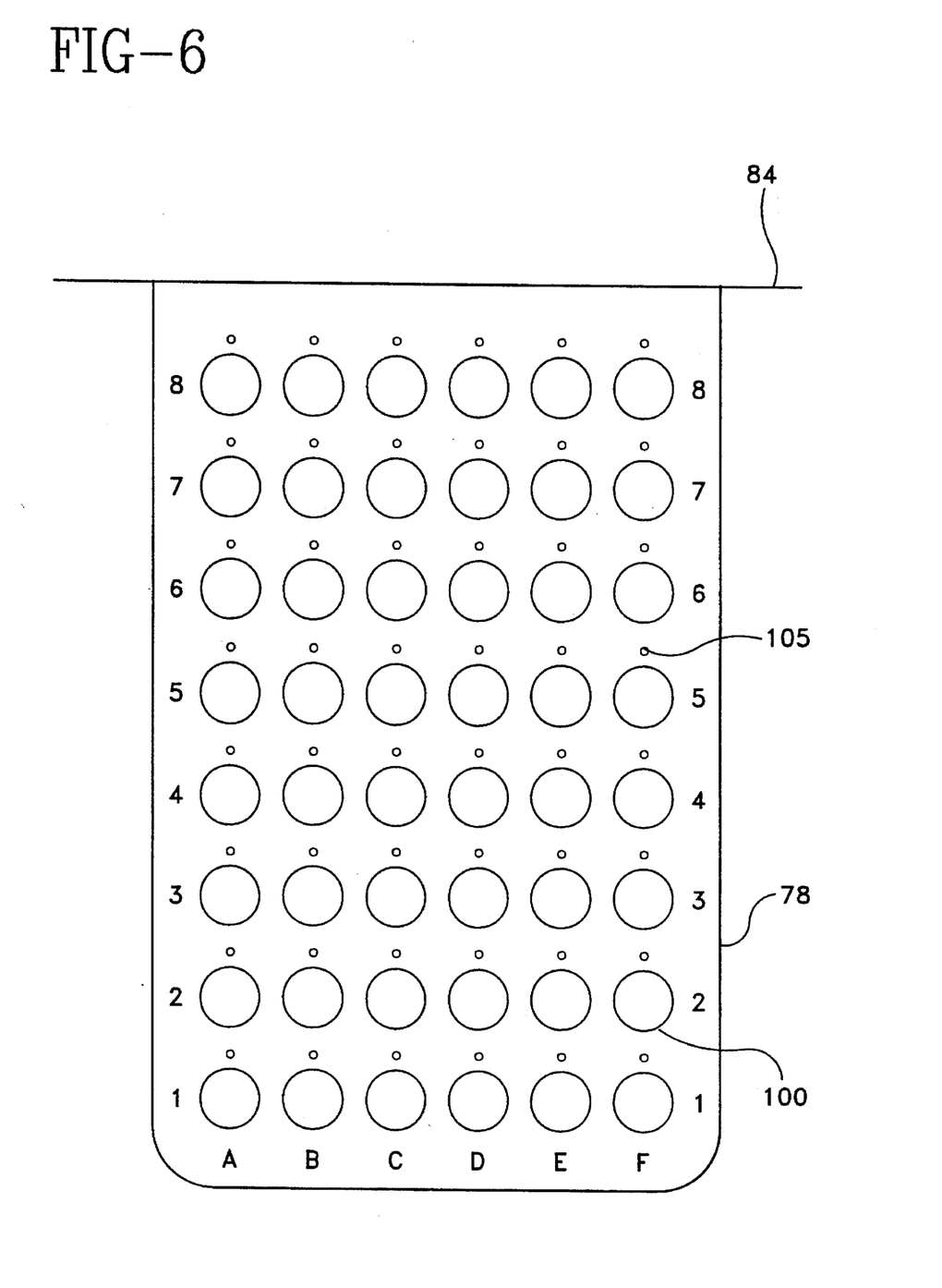
FIG. 6 shows a file drawer in the apparatus shown in FIG. 5.

FIG. 6 shows a top view of vial drawer 78 as it moves through door 84 out of incubator 82. As shown in FIG. 6, each vial station 100 is equipped with a plastic light guide 105 that can be illuminated from below by a corresponding LED 79. A steady-state light 79 is used to indicate that station 100 is ready for loading. Accordingly, a flashing light 79 is used to indicate that station 100 should be unloaded. In addition, a low flashing frequency may be used to indicate that vial 22 does not have bacterial growth therein and a much higher flashing rate may be used to indicate that vial 22 is positive.

Figure 7:
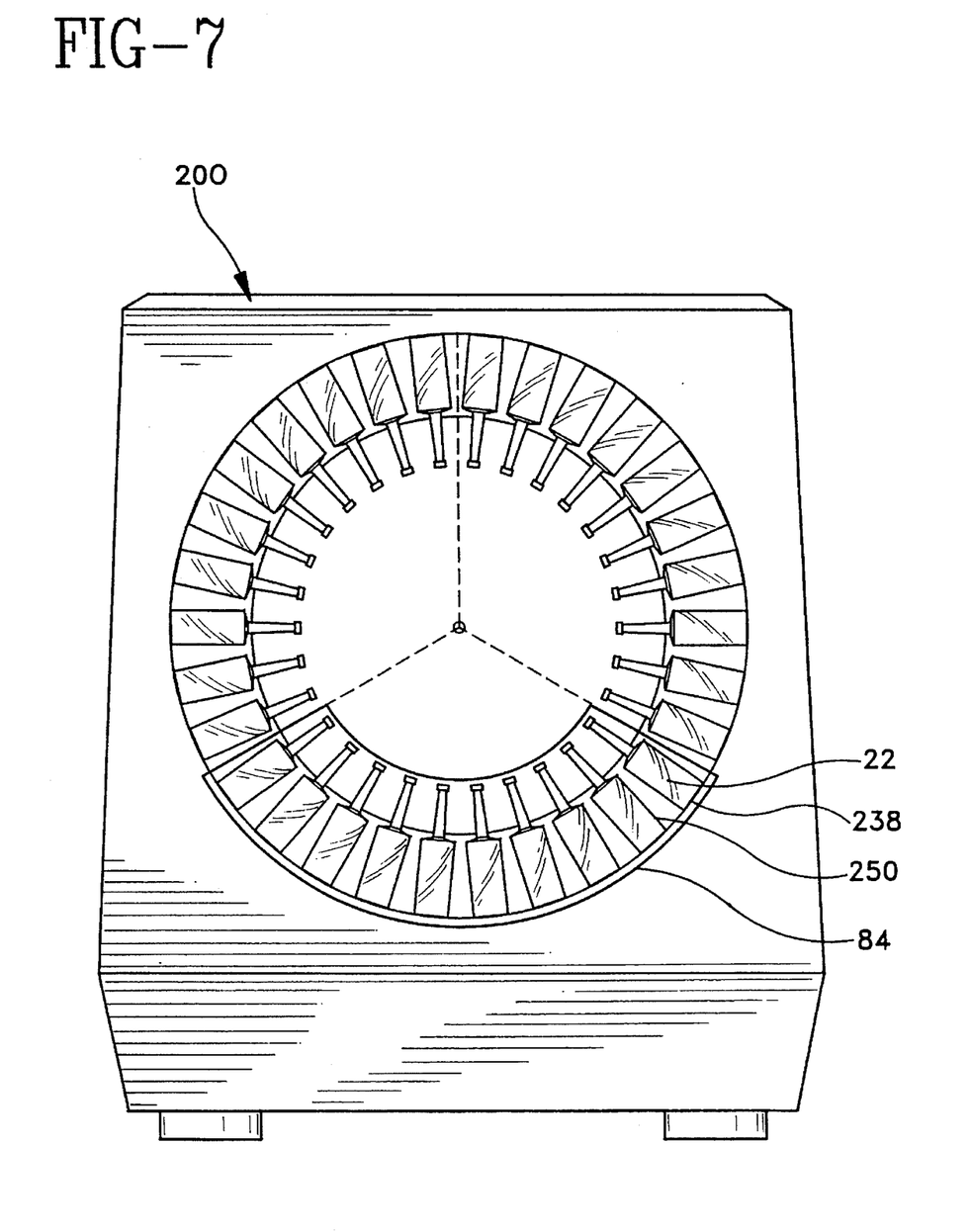
FIG. 7 shows a cross-sectional from view of another embodiment of a sub-compact blood culture apparatus, having a drum with three drawers.
Figure 8:
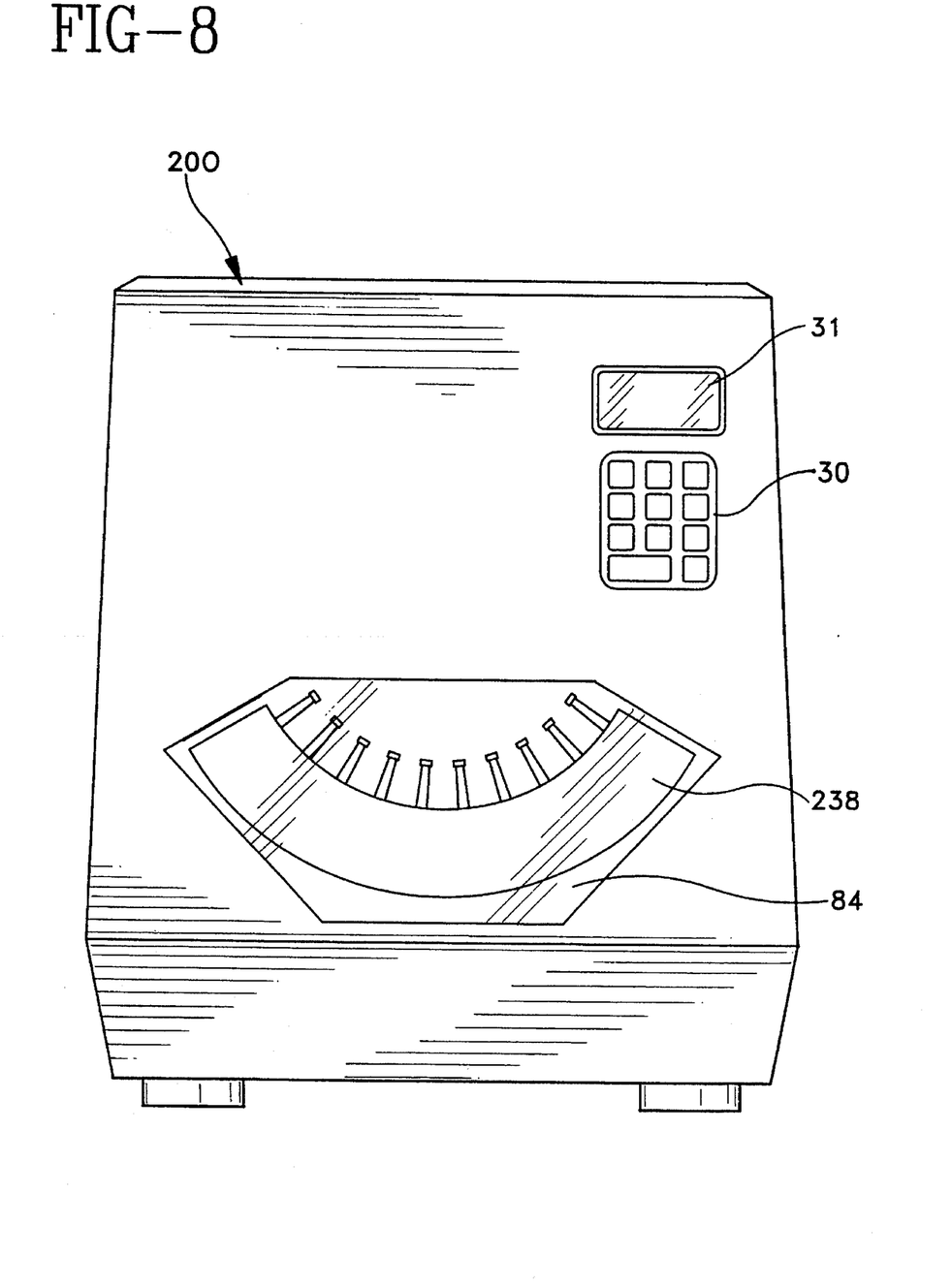
FIG. 8 shows a full front view of the apparatus shown in FIG. 7.

FIG. 7 shows yet another embodiment of a blood culture apparatus 200 having three drawers 238. Each drawer 238 containing eighty openings 250 for holding eighty vials 22 in a matrix consisting of ten rows and eight columns. As in the other embodiments, each drawer 238 is capable of being loaded and unloaded through door 84. FIG. 8 shows a full front view of apparatus 200 and more clearly shows door 84 and loaded drawer 238.

In the foregoing discussion, it is to be understood that the above-described embodiments are simply illustrative of a preferred apparatus for practicing the present invention, and that other suitable variations and modifications could be made to these embodiments and still remain within the scope of the present invention.

What is claimed is:

1. A sub-compact blood culture apparatus having an incubator comprising:

a drum rotatable about a horizontal axis having a plurality of drawers, each of said plurality of drawers including a top surface having a plurality of openings in which a corresponding plurality of vials are arranged;

a mechanism for rotating said drum about said axis;

at least one sensor station for detecting microorganisms within the plurality of vials received within said drum;

means for determining when one of said plurality of drawers is at a predetermined removal position; and means for removing said drawer at said predetermined removal position out of said drum so that said plurality of vials may be loaded into and unloaded from said plurality of openings in said top surface of said removed drawer.

2. A sub-compact blood culture apparatus according to claim 1, wherein:

each of said plurality of vials have a base and a neck; and said removed drawer is loaded with said base of each vial within said removed drawer and said neck of each vial extending from said top surface, so that said neck is closest to the axis of said drum when said removed drum is returned to said drum.

3. A sub-compact blood culture apparatus according to claim 1, wherein said removing means comprises a pair of rails upon which said removed drawer slides during removal from said drum.

4. A sub-compact blood culture apparatus according to claim 3, further comprising a door at said predetermined removal position for sealing said apparatus when in use and opening to permit said removed drawer to slide on said pair of rails for removal from said drum.

5. A sub-compact blood culture apparatus according to claim 1, further comprising an additional lower drawer with a number of illumination sources serving as load/unload indicators that indicate whether a corresponding vial is positive or not, and where said lower drawer moves together with the corresponding upper drawer during loading/unloading.

6. A sub-compact blood culture apparatus according to claim 5, wherein each illumination source indicates whether its corresponding opening contains one of said plurality of vials.

7. A sub-compact blood culture apparatus according to claim 1, wherein said drum includes three arcuate shaped drawers.

8. A sub-compact blood culture apparatus according to claim 7, wherein each of said arcuate shaped drawers includes a matrix of said plurality of openings having a plurality of rows and a plurality of columns, wherein one of said plurality of rows corresponds to said at least one sensor station for detecting microorganisms within the plurality of vials in said one row as each of said plurality of vials in said one row passes over said at least one sensor station.

9. A sub-compact blood culture apparatus according to claim 8, wherein:

each of said plurality of vials have a base and a neck; and said removed drawer is loaded with said base of each vial within said removed drawer and said neck of each vial extending from said top surface, so that said neck is closest to the axis of said drum when said removed drum is returned to said drum.

10. A sub-compact blood culture apparatus having an incubator comprising:

a drum rotatable about a horizontal axis having a plurality of arcuate shaped drawers, each of said plurality of arcuate shaped drawers including a top surface having a plurality of openings in which a corresponding plurality of vials are arranged, each of said plurality of vials having a base and a neck;

a mechanism for rotating said drum about said axis;

at least one sensor station for detecting microorganisms within the plurality of vials received within said drum;

means for determining when one of said plurality of arcuate shaped drawers is at a predetermined removal position; and means for removing said arcuate shaped drawer at said predetermined removal position out of said drum so that said plurality of vials may be loaded into said plurality of openings in said top surface of said removed drawer, whereby said removed drawer is loaded with said base of each vial within said removed drawer and said neck of each vial extending from said top surface, so that said neck is closest to the axis of said drum when said removed drum is returned to said drum.

* * * * *